United States Patent [19]

Torii et al.

[11] Patent Number: 4,713,452
[45] Date of Patent: Dec. 15, 1987

[54] PROCESS FOR PREPARATION OF AZETIDINONE DERIVATIVES

[75] Inventors: Sigeru Torii; Hideo Tanaka, both of Okayama; Michio Sasaoka, Tokushima; Seiryu Uto, Tokushima; Syozo Hayase, Tokushima, all of Japan

[73] Assignee: Otsuka Kagaku Kabushiki Kaisha, Osaka, Japan

[21] Appl. No.: 680,723

[22] Filed: Dec. 12, 1984

[30] Foreign Application Priority Data

Dec. 12, 1983 [JP] Japan .................. 58-234723

[51] Int. Cl.⁴ .................. C07D 205/08; C07B 45/00; C07F 9/65; C07F 7/10
[52] U.S. Cl. .................................... 540/358
[58] Field of Search .................. 260/245.4, 239 A; 540/358

[56] References Cited

U.S. PATENT DOCUMENTS 4,147,864  4/1979  Woodward ................ 260/239 A

FOREIGN PATENT DOCUMENTS 2261761  9/1975  France .
1503638  3/1978  United Kingdom .

OTHER PUBLICATIONS

Lo et al, J.A.C.S. 94, 8253 (1972).
Sheehan, J. Organic Chem. 42, 4045 (1977).
Barton/Ollis, Comprehensive Organic Chemistry, vol. 3 (1979), pp. 209, 289, and 301.
Kill, Accounts Chem. Res. 1 (1968), pp. 58-64.
Allan, J. Chem. Soc. Perkin I (1974), pp. 1456-1459.
Van Leasen, Tetrahedron Letters, 12 (1970), pp. 967-970.
Houben-Weyl, Meth. Org. Chem., vol. 9, (1955), pp. 72-73.
Fugisawa, Chemical Abstracts, vol. 98, No. 23, 6 Jun. 1983, p. 620, abstract no. 197890t.

*Primary Examiner*—Mark L. Berch
*Attorney, Agent, or Firm*—Armstrong, Nikaido, Marmelstein & Kubovcik

[57] ABSTRACT

A process for preparing an azetidinone derivative represented by the formula

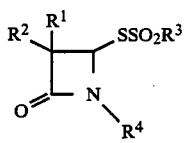

(I)

wherein $R^1$ is hydrogen, halogen or lower alkoxy, $R^2$ is hydrogen, halogen, lower alkoxy, amino or a group

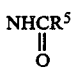

(in which $R^5$ is substituted or unsubstituted phenyl, substituted or unsubstituted phenylmethyl, substituted or unsubstituted phenoxymethyl, or substituted or unsubstituted benzoyl), or $R^1$ and $R^2$, when taken together, are carbonyl, $R^3$ is substituted or unsubstituted phenyl, and $R^4$ is hydrogen, optionally substituted hydrocarbon residue or acyl, silyl, sulfonyl or phosphonyl derived from inorganic acid or organic acid, the process comprising reacting a dithioazetidinone derivative represented by the formula

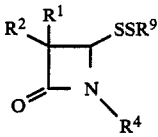

(VI)

wherein $R^1$, $R^2$ and $R^4$ are as defined above and $R^9$ is substituted or unsubstituted, nitrogen-containing aromatic heterocyclic residue with a compound represented by the formula $$R^3SO_2CN \qquad (VII)$$

wherein $R^3$ is defined above.

7 Claims, No Drawings

PROCESS FOR PREPARATION OF AZETIDINONE DERIVATIVES

This invention relates to a process for preparing azetidinone derivatives.

The azetidinone derivatives prepared by the process of the present invention are represented by the formula

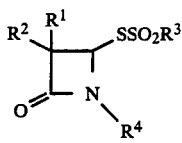

wherein $R^1$ is hydrogen, halogen or lower alkoxy, $R^2$ is hydrogen, halogen, lower alkoxy, amino or a group

(in which $R^5$ is substituted or unsubstituted phenyl, substituted or unsubstituted phenylmethyl, substituted or unsubstituted phenoxymethyl, or substituted or unsubstituted benzoyl), or $R^1$ and $R^2$, when taken together, are carbonyl, $R^3$ is substituted or unsubstituted phenyl, and $R^4$ is hydrogen, optionally substituted hydrocarbon residue or acyl, silyl, sulfonyl or phosphonyl derived from inorganic acid or organic acid.

The azetidinone derivatives of the formula (I) are useful as the intermediates for synthesizing β-lactam antibiotics and can be made into a variety of β-lactam antibiotics depending on the selection of substituents. For example, an azetidinone derivative of the formula (I) wherein $R^4$ is a group

(in which $R^6$ is hydrogen or carbonxy protecting group) can be converted into a cephalosporin compound of the formula (III) by the process disclosed in Tetrahedron Letters, 23, 2187 (1982) which is shown in the following reaction scheme.

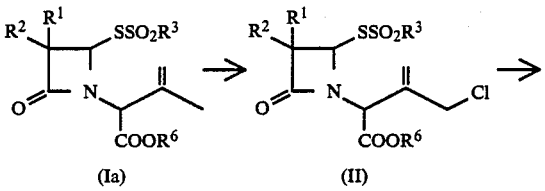

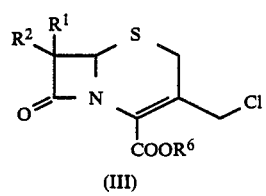

An azetidinone derivative of the formula (I) wherein $R^4$ is hydrogen, silyl, sulfonyl or phosphonyl can be made into various monocyclic β-lactam antibiotics.

Conventional processes for preparing azetidinone derivatives of the formula (I) are described, for example, in Japanese Unexamined Patent Publication (Kokai) No. 129,590/1975. This process comprises, as indicated below by a reaction equation, reacting an azetidinone derivative of the formula (IV) with a heavy metal salt of sulfinic acid of the formula (V) to obtain an azetidinone derivative of the formula (Ib).

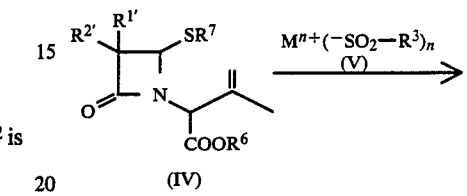

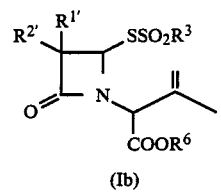

In the foregoing reaction equation, $R^3$ and $R^6$ are as defined above, $R^{1'}$ is hydrogen, $R^{2'}$ is amino or a group -$NHR^8$ (wherein $R^8$ is acyl), $R^7$ is an aromatic hetrocyclic group, aliphatic thioacyl group, aromatic thioacyl group, aromatic aliphatic thioacyl group or alicyclic thioacyl group, M is heavy metal such as copper, silver, mercury, tin or the like and n is the valence of heavy metal. However, the above process, when commercially carried out, involves the disadvantage of using a heavy metal salt of sulfinic acid of the formula (V) which is harmful or expensive.

It is an object of the present invention to provide a commercially advantageous process for preparing the azetidinone derivatives of the formula (I).

It is another object of the invention to provide a process for preparing the azetidinone derivative of the formula (I) without use of a heavy metal salt of sulfinic acid which is harmful or expensive.

It is a further object of the invention to provide a process for preparing the azetidinone derivative of the formula (I) with a high purity and in a high yield by carrying out a simple procedure.

These objects and other features of the present invention will become more apparent from the following description.

According to the present invention, the azetidinone derivative of the formula (I) can be prepared by reacting a dithioazetidinone derivative represented by the formula

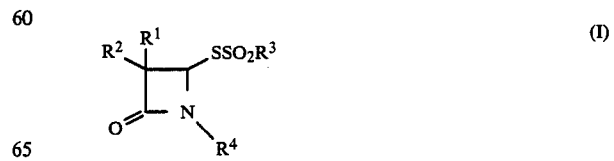

wherein $R^1$, $R^2$ and $R^4$ are as defined above and $R^9$ is substituted or unsubstituted, nitrogen-containing aromatic heterocyclic residue with a compound represented by the formula $$R^3SO_2CN \qquad (VII)$$

wherein $R^3$ is as defined above.

Examples of the halogen atoms represented by $R^1$ in the formulae (I) and (VI) are F, Cl, Br, I and the like. Exemplary of the lower alkoxy groups represented by $R^1$ are those having 1 to 4 carbon atoms such as methoxy, ethoxy, propoxy, isopropoxy, butoxy, tert-butoxy, etc.

Examples of the halogen atoms represented by $R^2$ in the formulae (I) and (VI) are F, Cl, Br, I and the like. Illustrative of the lower alkoxy groups represented by $R^2$ are those having 1 to 4 carbon atoms such as methoxy, ethoxy, propoxy, isopropoxy, butoxy and tert-butoxy, etc. Examples of the substituted phenyl groups represented by $R^5$ are phenyl substituted with 1 to 3 $C_1$-$C_4$ alkyl groups such as tolyl; phenyl substituted with 1 to 3 halogen atoms such as 4-chlorophenyl, 2,4-dichlorophenyl, 2,4,6-trichlorophenyl, 4-bromophenyl and 2,4-dibromophenyl; phenyl substituted with 1 to 3 $C_1$-$C_4$ alkoxy groups such as 4-methoxyphenyl, 2,4-dimethoxyphenyl and 3,4,5-trimethoxyphenyl ; phenyl substituted with 1 to 3 nitro groups such as 4-nitrophenyl and 2,4-dinitrophenyl; etc. Examples of the substituted phenylmethyl groups represented by $R^5$ are phenylmethyl substituted with 1 to 3 $C_1$-$C_4$ alkyl groups on the phenyl ring such as tolylmethyl; phenylmethyl substituted with 1 to 3 halogen atoms on the phenyl ring such as 4-chlorophenylmethyl, 2,4-dichlorophenylmethyl, 2,4,6-trichlorophenylmethyl, 4-bromophenylmethyl and 2,4-dibromophenylmethyl; phenylmethyl substituted with 1 to 3 $C_1$-$C_4$ alkoxy groups on the phenyl ring such as 4-methoxyphenylmethyl, 2,4-dimethoxyphenylmethyl and 3,4,5-trimethoxyphenylmethyl; phenylmethyl substituted with 1 to 3 nitro groups on the phenyl ring such as 4-nitrophenylmethyl and 2,4-dinitrophenylmethyl; phenylmethyl having methylene substituted with halogen, hydroxy, hydroxyimino, $C_1$-$C_4$ alkoxyimino, amino or the like such as phenyldichloromethyl, phenylhydroxymethyl, phenylhydroxyiminomethyl, phenylmethoxyiminomethyl, phenylaminomethyl and phenylacetoxymethyl; etc. Examples of the substituted phenoxymethyl groups represented by $R^5$ are phenoxymethyl substituted with 1 to 3 $C_1$-$C_4$ alkyl groups on the phenyl ring such as tolyloxymethyl; phenoxymethyl substituted with 1 to 3 halogen atoms on the phenyl ring such as 4-chlorophenoxymethyl, 2,4-dichlorophenoxymethyl, 2,4,6-trichlorophenoxymethyl, 4- bromophenoxymethyl and 2,4-dibromophenoxymethyl; phenoxymethyl substituted with 1 to 3 $C_1$-$C_4$ alkoxy groups on the phenyl ring such as 4-methoxyphenoxymethyl, 2,4-dimethoxyphenoxymethyl and 3,4,5-trimethoxyphenoxymethyl; phenoxymethyl substituted with 1 to 3 nitro groups on the phenyl ring such as 4-nitrophenoxymethyl and 2,4-dinitrophenoxymethyl; etc. Examples of the substituted benzoyl groups represented by $R^5$ are benzoyl substituted with 1 to 3 $C_1$-$C_4$ alkyl groups on the phenyl ring such as toluoyl; benzoyl substituted with 1 to 3 halogen atoms on the phenyl ring such as 4-chlorobenzoyl, 2,4-dichlorobenzoyl, 2,4,6-trichlorobenzoyl, 4-bromobenzoyl and 2,4-dibromobenzoyl; benzoyl substituted with 1 to 3 $C_1$-$C_4$ alkoxy groups on the phenyl ring such as 4-methoxybenzoyl, 2,4-dimethoxybenzoyl and 3,4,5-trimethoxybenzoyl; benzoyl substituted with 1 to 3 nitro groups on the phenyl ring such as 4-nitrobenzoyl and 2,4-dinitrobenzoyl; etc.

Examples of the substituted phenyl represented ny $R^3$ in the formulae (I) and (VII) are phenyl substituted with 1 to 3 $C_1$-$C_4$ alkyl groups such as tolyl and xylyl; phenyl substituted with 1 to 3 halogen atoms such as 4-chlorophenyl, 2,4-dichlorophenyl, 2,4,6-trichlorophenyl, 4-bromophenyl and 2,4-dibromophenyl; phenyl substituted with 1 to 3 $C_1$-$C_4$ alkoxy groups such as 4-methoxyphenyl, 2,4-dimethoxyphenyl and 3,4,5-trimethoxyphenyl; phenyl substituted with 1 to 3 nitro groups such as 4-nitrophenyl and 2,4-dinitrophenyl; etc.

The groups represented by $R^4$ in the formulae (I) and (VI) are hydrogen, acyl, silyl, sulfonyl and phosphonyl derived from inorganic or organic acid, and optionally substituted hydrocarbon residue. Of these groups, the optionally substituted hydrocarbon residue is preferred. Exemplary of the substituted hydrocarbon residue are groups

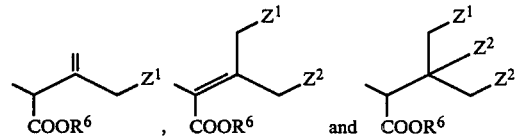

wherein $R^6$ is hydrogen or carboxy protecting group. The wide range of carboxy protecting groups as disclosed in Theodora W. Greene: "Protective Groups in Organic Synthesis," Chapter 5 are usable in the present invention. Typical examples of the groups are phenyl $C_1$-$C_4$ alkyl optionally having 1 to 3 substituents, e.g., $C_1$-$C_4$ alkoxy, halogen, methylenedioxy, $C_1$-$C_4$ alkyl or nitro on the phenyl ring such as benzyl, p-methoxybenzyl, trimethoxybenzyl, trimethoxydichlorobenzyl, piperonyl, diphenylmethyl, bis(p-methoxyphenyl)methyl, ditolyl methyl, phenyl-p-methoxyphenylmethyl, α-p-methoxyphenylmethyl, trityl, α-diphenylethyl, p-nitrobenzyl, o-nitrobenzyl and o,p-dinitrobenzyl; $C_1$-$C_4$ alkyl which may have at least substituent selected from halogen, phenyl substituted with 1 to 3 $C_1$-$C_4$ alkoxy groups, benzoyl, benzoyl substituted with 1 to 3 halogen atoms on the phenyl ring, $C_1$-$C_4$ alkoxy, $C_1$-$C_4$ alkoxy substituted with 1 to 3 $C_1$-$C_4$ alkoxy groups, benzyloxy, $C_1$-$C_4$ alkanoyl and $C_1$-$C_4$ alkoxycarbonyl, such as tert-butyl, trichloroethyl, α-p-methoxyphenyl-β-trichloroethyl, phenacyl, p-bromophenacyl, methoxymethyl, isopropoxymethyl, methoxyethoxymethyl, benzyloxymethyl and 1-methoxycarbonyl-2-oxopropyl; cumyl; fluorenyl; etc. $Z^1$ and $Z^2$ are the same or different and are each hydrogen, halogen, sulfur-containing group, oxygen-containing group, nitrogen-containing group or the like. Examples of the substituents represented by $Z^1$ and $Z^2$ are halogen such as bromine, chlorine and fluorine; sulfur-containing groups, e.g., $C_1$-$C_4$ alkylthio such as methylthio and ethylthio, phenylthio optionally substituted with 1 to 5 nitro groups or halogen atoms on the phenyl ring such as phenylthio, p-nitrophenylthio and pentachlorophenylthio, 2-pyridylthio, 2-benzothiadiazolylthio, 1,3,4-thiadiazol-5ylthio, 2-substituted-1,3,4-thiadiazol-5-ylthio, 1,2,3,4-tetrazol-5-ylthio, 1-substituted-1,2,3,4-tetrazol-5ylthio, O-ethyldithiocarbonate, N,N-diethyldithiocarbamate, phenylsulfonyl and p-methylphenylsulfonyl; oxygen containing groups, e.g., hydroxy, $C_1$-$C_4$ alkoxy such as methoxy and ethoxy, $C_1$-$C_4$ acyloxy such as acetoxy, benzoyloxy, nitrosoxy, nitriloxy, diphenylphosphonyloxy, methanesulfonate, N-morphonyl and diphenylmethyloxy; nitrogen-containing groups, e.g., di($C_1$-$C_4$ alkyl)amino such as dimethylamino, and piperidin-1yl; etc.

Examples of the substituted or unsubstituted nitrogen-containing aromatic heterocyclic residue represented by $R^9$ in the formula (VI) are those optionally having 1 to 3 substituents, e.g., with $C_1$-$C_4$ alkyl, phenyl, $C_1$-$C_4$ alkoxy, nitro or halogen, such as thiazol-2-yl, 4-methylthiazol-2-yl, 5-methylthiazol-2-yl, 4-phenylthiazol-2-yl, 5-phenylthiazol-2-yl, thiadiazol-2-yl, 5-methylthiadiazol-2-yl, 5-phenylthiadiazol-2-yl, 5-methoxycarbonylthiadiazol-2-yl, benzothiazol-2-yl, 4-methylbenzothiazol-2-yl, 6-methylbenzothiazol-2-yl, 5-methoxybenzothiazol 2-yl, 6-nitrobenzothiazol-2-yl, 5-chlorobenzothiazol-2-yl, benzoxazol-2-yl, 4-methylbenzoxazol-2-yl, 6-phenylbenzoxazol-2-yl, 5-methoxybenzoxazol-2-yl, 5-chlorobenzoxazol-2-yl, benzimidazol-2-yl, 5-methylbenzimidazol-2-yl, 6-chlorobenzoimidazol-2-yl, pyrimidin-2-yl, 5-methylpyrimidin-2-yl and 2-pyridyl, etc.

The dithioazetidinone derivatives of the formula (VI) used as one of the starting materials in the present invention are known and can be synthesized by various processes. The synthesizing processes using penicillin are disclosed, for example, in Tetrahedron Letters, 3001 (1973), Japanese Examined Patent Publication (Kokoku) No.14665/1981; Japanese Unexamined Patent Publications (Kokai) Nos. 29587/1982, 59896/1982, 183793/1982 and 183794/1982; and The Collection of Drafted Research Reports for The 9th International Convention on Heterocycle, page 300 (1983). The derivatives of the formula (VI) can be produced also by a combination of processes described in these publications. These known processes are shown, for example, in the following reaction scheme.

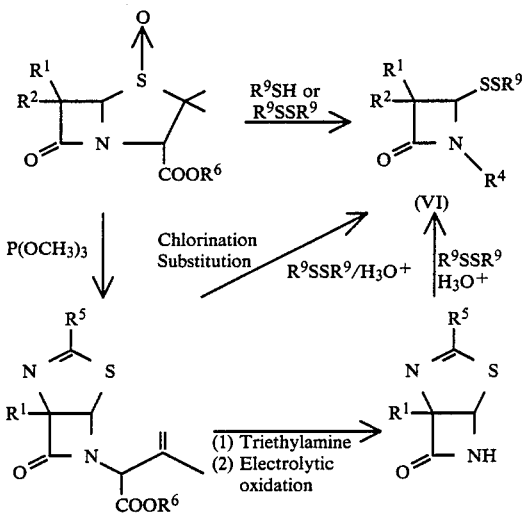

In the above reaction scheme, $R^1$, $R^2$, $R^4$, $R^5$, $R^6$ and $R^9$ are as defined above.

However, the dithioazetidinone derivatives of the formula (VI) as used in the present invention are not limited to those producible by these processes. An extensive range of dithioazetidinone derivatives of the formula (VI) produced by various processes including those other than the foregoing processes can be used as the starting material in the present invention.

The compounds of the formula (VII), namely the other starting material used in the present invention, are also known. The compound of the formula (VII) can be synthesized, for example, by the process as set forth in Tetrahedron Letters, 3351 (1969) or can be produced in the reaction system of the present invention using the corresponding sulfonyl halide and alkali metal cyanide.

According to the present invention, the dithioazetidinone derivative of the formula (VI) is reacted with the compound of the formula (VII) usually in a suitable solvent. Examples of the solvent which can be used in the present invention is not particularly limited as far as the solvent is capable of dissolving the compound of the formula (VI) and the compound of the formula (VII). Since these compounds need not be completely dissolved in the present invention, even solvents capable of partially dissolving them are usable. Useful solvents include organic solvents used singly or in conjunction with water. Examples of suitable organic solvents are ketones such as acetone, methyl ethyl ketone, diethyl ketone and methyl isobutyl ketone; esters such as methyl formate, ethyl formate, propyl formate, methyl acetate, ethyl acetate, propyl acetate, methyl propionate and ethyl propionate; aromatic hydrocarbons such as benzene, toluene and xylene; halogenated hydrocarbons such as dichloromethane, dibromomethane, chloroform, bromoform, carbon tetrachloride, dichloroethane, dibromoethane and trichloroethane; ethers such as diethyl ether, dipropyl ether, dibutyl ether, tetrahydrofuran and dioxane; nitroalkanes such as nitromethane, nitroethane and nitropropane; nitriles such as acetonitrile, propionitrile, butyronitrile and valeronitrile; alcohols such as methanol, ethanol, propanol, isopropanol and butanol; etc. These organic solvents can be used singly or at least two of them are usable in admixture. The amount of the solvent is usually about 1 to about 400 times, preferably about 1 to about 200 times, more preferably about 1 to about 50 times, the weight of the compound of the formula (VI).

The proportions of the compounds of the formulae (VI) and (VII) used in the present invention are not particularly limited and can be suitably determined over a wide range. Usually about 1 to about 5 moles, preferably about 1 to about 2 moles, of the compound of the formula (VII) is used per mole of the compound of the formula (VI).

The reaction of the present invention can be usually carried out at a temperature ranging from about −20° C. to the temperature at which the solvent used is refluxed. The reaction temperature ranges preferably from 0 to the solvent-refluxing temperature, more preferably about 20° C. to the solvent-refluxing temperature. The reaction time in the present invention varies depending on the reaction temperature, kinds of the compounds of the formulae (VI) and (VII) and other conditions, but usually ranges from about 0.1 to about 15 hours.

In the present invention, it is preferred to incorporate into the reaction system at least one kind of catalyst selected from a sulfinic acid of the formula $$R^3SO_2H \qquad (VIII)$$

wherein $R^3$ is as defined above or a salt thereof, a thiol of the formula $$R^9SH \qquad (IX)$$

wherein $R^9$ is as defined above or a salt thereof, and a nucleophilic compound capable of producing $R^3SO_2^\ominus$ when reacted with the compound (VII). The presence fo the foregoing catalyst in the reaction system results in the production of the desired compound (I) of higher purity in higher yields.

Examples of the substituted or unsubstituted phenyl represented by $R^3$ in the sulfinic acid (VIII) are the same as those exemplified above. Examples of the sulfinic acid (VIII) as used above are benzenesulfinic acid, tolylsulfinic acid, xylylsulfinic acid, 4-chlorophenylsulfinic acid, 2,4-dichlorophenylsulfinic acid, 2,4,6-trichlorophenylsulfinic acid, 4-bromophenylsulfinic acid, 2,4-dibromophenylsulfinic acid, 4-methoxyphenylsulfinic acid, 2,4-dimethoxyphenylsulfinic acid, 3,4,5-trimethoxyphenylsulfinic acid, 4-nitrophenylsulfinic acid, 2,4--dinitrophenylsulfinic acid, etc. Examples of the salt of the sulfinic acid (VIII) as used above are salts of alkali metals such as lithium, sodium, potassium and rubidium, salts of alkaline earth metals such as magnesium, calcium, strontium and barium, ammonium salts such as ammonium, tetra ($C_1$–$C_4$ alkyl)ammonium, e.g., tetramethylammonium, tetraethylammonium and trimethyl ethyl ammonium, pyridium salt, etc. Of these salts, an alkali metal salt is preferably used. Preferred examples of the alkali metal salts are sodium benzenesulfinate, potassium benzenesulfinate, lithium benzenesulfinate, rubidium benzenesulfinate, sodium tolylsulfinate, potassium tolylsulfinate, sodium xylylsulfinate, sodium 4-chlorophenylsulfinate, potassium 4-chlorophenylsulfinate, sodium 2,4-dichlorophenylsulfinate, sodium 2,4,6-trichlorophenylsulfinate, sodium 4-bromophenylsulfinate, sodium 2,4-dibromophenylsulfinate, sodium 4-methoxyphenylsulfinate, potassium 4-methoxyphenylsulfinate, sodium 2,4-dimethoxyphenylsulfinate, sodium 3,4,5-trimethoxyphenylsulfinate, sodium 4-nitrophenylsulfinate, potassium 4-nitrophenylsulfinate, sodium 2,4-dinitrophenylsulfinate, potassium 2,4-dinitrophenylsulfinate, etc.

Examples of the substituted or unsubstituted, nitrogen-containing aromatic heterocyclic residue represented by $R^9$ in the thiol (IX) are the same as those exemplified above. Examples of the thiol (IX) as used above are 2-thiazole thiol, 2-(4-methyl)thiazole thiol, 2-(5-methyl)thiazole thiol, 2-(4-phenyl)thiazole thiol, 2-(5-phenyl)thiazole thiol, 2-thiadiazole thiol, 2-(5-methyl)thiadiazole thiol, 2-(5-phenyl)thiadiazole thiol, 2-(5-methoxycarbonyl)thiadiazole thiol, 2-benzothiazole thiol, 2-(4-methyl)benzothiazole thiol, 2-(6-methyl)benzothiazole thiol, 2-(5-methoxy)benzothiazole thiol, 2-(4-nitro)benzothiazole thiol, 2-(6-nitro)benzothiazole thiol, 2-(5-chloro)benzothiazole thiol, 2-benzoxazole thiol, 2-(4-methyl)benzoxazole thiol, 2-(6-phenyl)benzoxazole thiol, 2-(5-methoxy) benzimidazole thiol, 2-(6-methyl)benzimidazole thiol, 2-benzimidazole thiol, 2-(6-methyl)benzimidazole thiol, 2-(6-chloro)benzimidazole thiol, 2-pyrimidine thiol, 2-(5-methyl)pyrimidine thiol, 2-pyridyl thiol, etc. Examples of the salt of the thiol (IX) as used above are salts of alkali metals such as lithium, sodium, potassium and rubidium, salts of alkaline earth metals such as magnesium, calcium, strontium and barium, ammonium salts such as ammonium, tetra($C_1$–$C_4$ alkyl) ammonium, e.g., tetramethylammonium, tetraethylammonium and trimethyl ethyl ammonium, pyridium salt, etc. Of these salts, an alkali metal salt is preferably used. Preferred examples of the alkali metal salts are sodium 2-thiazole thiolate, sodium 2-(4-methyl)thiazole thiolate, sodium 2-(5-methyl)thiazole thiolate, sodium 2-(4-phenyl)- thiazole thiolate, sodium 2-(5-phenyl)thiazole thiolate, sodium 2-thiadiazole thiolate, sodium 2-(5-methyl)- thiadiazole thiolate, sodium 2-(5-phenyl) thiadiazole thiolate, sodium 2-(5-methoxycarbonyl) thiadiazole thiolate, sodium 2-benzothiazole thiolate, sodium 2-(6-methyl)benzothiazole thiolate, sodium 2-(5-methoxy)- benzothiazole thiolate, sodium 2-(4-nitro) benzothiazole thiolate, sodium 2-(6-nitro)benzothiazole thiolate, sodium 2-(5-chloro)benzothiazole thiolate, sodium 2-benzoxazole thiolate, sodium 2-(4-methyl)benzoxazole thiolate, sodium 2-(6-phenyl)benzoxazole thiolate, sodium 2-(5-methoxy)benzoxazole thiolate, sodium 2-(5-chloro)benzoxazole thiolate, sodium 2-benzimidazole thiolate, sodium 2-(6-methyl)benzimidazole thiolate, sodium 2-(6-chloro)benzimidazole thiolate, sodium 2-pyrimidine thiolate, sodium 2-(5-methyl)pyrimidine thiolate, sodium 2-pyridyl thiolate, potassium 2-benzothiazole thiolate, potassium 2-(4-methyl)benzothiazole thiolate, potassium 2-(6-methyl)benzothiazole thiolate, potassium 2-(6-nitro)benzothiazole thiolate, potassium 2-(5-methoxy)benzothiazole thiolate, potassium 2-(5-methyl)thiadiazole thiolate, lithium 2-benzothiazole thiolate, rubidium 2-benzothiazole thiolate, etc.

Examples of useful nucleophilic compounds are water; alkali metal hydroxides such as lithium hydroxide, sodium hydroxide and potassium hydroxide; alcohols having 1 to 4 carbon atoms such as methanol, ethanol, propanol, isopropanol, butanol and inorganic or organic salts thereof; phenols such as phenol, cresol, p-methoxyphenol, p-nitrophenol and inorganic or organic salts thereof; thiols other than the compounds (IX) such as methanethiol, ethanethiol, propanethiol, thiophenol, thiocresol, p-nitrothiophenol and inorganic or organic salts thereof; sulfinic acids other than the compounds (VIII) such as methanesulfinic acid, ethanesulfinic acid, propanesulfinic acid and inorganic or organic salts thereof; carboxylic acids such as acetic acid, propionic acid and inorganic or organic salts thereof; etc. When an alcohol having 1 to 4 carbon atoms is used as a solvent, no catalyst is required because the alcohol acts as a nucleophilic compound.

The reaction of the present invention with the reaction system containing the aforesaid catalyst is shown in the following reaction equation.

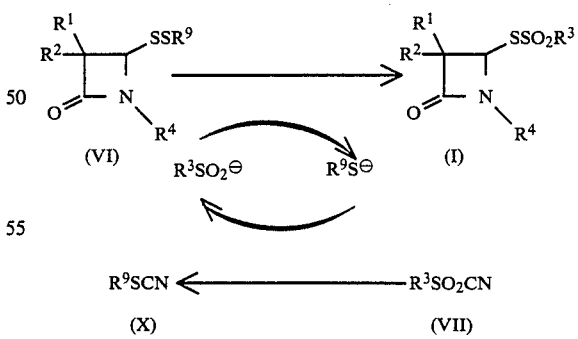

In the foregoing reaction equation, $R^1$, $R^2$, $R^3$, $R^4$ and $R^9$ are as defined above.

When at least one molecule of $R^3SO_2^\ominus$ or $R^9S^\ominus$ is present in the reaction system, the catalytic reaction as illustrated above can proceed between the compound (VI) and the compound (VII), thereby giving a compound (I).

More specifically, when a sulfinic acid (VIII) or a salt thereof is used as a catalyst, the sulfinic acid (VIII) or the salt thereof is reacted with a compound (VI) to form a compound (I) and a thiol (IX) or a salt thereof. The thiol (IX) or the salt thereof thus obtained is reacted with a compound (VII), producing a compound (X), respectively and regenerating a sulfinic acid (VIII) or a salt thereof. The regenerated sulfinic acid (VIII) or the salt thereof is reacted with a compound (VI).

When a thiol (IX) or a salt thereof is used as a catalyst, the thiol (IX) or the salt thereof is reacted with a compound (VII), affording a sulfinic acid (VIII) or a salt thereof and a compound (X). The sulfinic acid (VIII) or the salt thereof is reacted with a compound (VI), producing a compound (I) and regenerating a thiol (IX) or a salt thereof.

When a sulfinic acid (VIII) or a salt thereof is used in conjunction with a thiol (IX) or a salt thereof, the foregoing reactions simultaneously proceed.

When the above-mentioned nucleophilic compound is used as a catalyst, the reaction proceeds in the same manner as in use of the sulfinic acid (VIII) or the salt thereof as a catalyst.

While reaction can proceed with a system containing one molecule of the catalyst, usually about 0.0001 to about 0.1 mole, preferably about 0.001 to about 0.05 mole, of the catalyst is used per mole of the compound (VI).

After the completion of the reaction, the azetidinone derivative (I) of the present invention can be separated from the reaction mixture by conventional methods such as filtration, centrifugation, distillation, extraction, etc. The azetidinone derivative (I) thus obtained is substantially pure, but can be easily purified by recrystallization, column chromatography or like means if further purification is needed.

According to the present invention, a desired compound (I) of high purity can be prepared in high yields without use of expensive or harmful heavy metal salt of sulfinic acid by carrying out a simple procedure The present invention will be described below in more detail with reference to the following Examples to which, however, the present invention is limited in no way and in which the code Ph referes to phenyl.

EXAMPLE 1

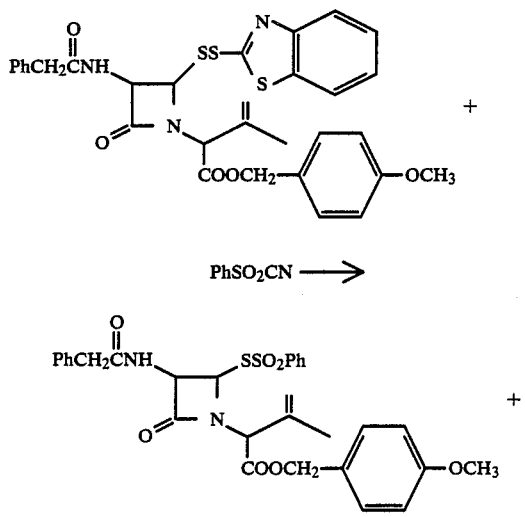

PhSO₂CN ⟶

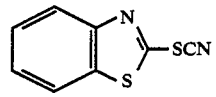

A 560 mg quantity of p-methoxybenzyl 2-[3-phenylactamido-4-(2-benzothiazolyldithio)-2-azetidinon-1-yl]-3-methyl-3-butenoate and 302 mg of benzenesulfonyl cyanide were dissolved in 5 ml of acetone. To the solution was added 0.5 ml of water and the mixture was reacted with heating for 1.5 hours while refluxing the acetone. The acetone was distilled off undre reduced pressure and the residue was dissolved in 10 ml of benzene. The benzene solution was washed with water, dried over Na₂SO₄ and concentrated under reduced pressure. The resulting residue was purified by silica gel column chromatography, giving p-methoxybenzyl 2-(3-phenylacetamido-4-benzenesulfonylthio-2-azetidinon-1-yl)-3-methyl-3-butenoate in a yield of 95%. The NMR spectrum data of the compound thus obtained were identical with those of the desired compound. Table 2 shows the NMR spectrum data of the compound.

EXAMPLE 2

A 529 mg quantity of p-methoxybenzyl 2-[3-phenylacetamido-4-(2-benzothiazolyldithio)-2-azetidinon-1-yl]-3-methyl-3-butenoate and 157 mg of benzenesulfonyl cyanide were dissolved in 5 ml of ethyl acetate. To the solution was added 0.5 ml of water and the mixture was reacted with heating at 80° C. for 1 hour. The reaction mixture was cooled to room temperature and was washed with water, dried over Na₂SO₄ and concentrated under reduced pressure. The residue was purified by silica gel column chromatography, giving p-methoxybenzyl 2-(3-phenylacetamido-4-benzenesulfonylthio-2-azetidinon-1-yl)-3-methyl-3-butenoate in a yield of 88%. The NMR spectrum data of the compound thus obtained were identical with those of the compound prepared in Example 1.

EXAMPLE 3

A 478 mg quantity of p-methoxybenzyl 2-[3-phenylacetamido-4-(2-benzothiazolyldithio)-2-azetidinon-1-yl]-3-methyl-3-butenoate and 155 mg of benzenesulfonyl cyanide were dissolved in 5 ml of chloroform. To the solution was added 0.25 ml of water and the mixture was reacted with heating for 1.5 hours while refluxing the chloroform. The reaction mixture was cooled to room temperature, washed with water, dried over Na₂SO₄ and concentrated under reduced pressure. The residue was purified by silica gel column chromatography, giving p-methoxybenzyl 2-(3-phenylacetamido-4-benzenesulfonylthio-2-azetidinon-1-yl)-3-methyl-3-butenoate in a yield of 89%. The NMR spectrum data of the compound thus obtained were identical with those of the compound produced in Example 1.

EXAMPLE 4

A 542 mg quantity of p-methoxybenzyl 2-[3-phenylacetamido-4-(2-benzothiazolyldithio)-2-azetidinon1-yl]-3-methyl-3-butenoate and 176 mg of benzenesulfonyl cyanide were dissolved in 5 ml of acetonitrile. To the solution was added 0.25 ml of water and the mixture was reacted with heating at 67° C. for 1.5 hours. The acetonitrile was distilled off under reduced pressure and the residue was dissolved in 10 ml of benzene. The benzene solution was washed with water, dried over Na₂SO₄ and concentrated under reduced pressure. sure. The residue was purified by silica gel column chromatography, giving p-methoxybenzyl 2-(3-phenylacetamido 4 benzenesulfonylthio-2-azetidinon-1-yl)-3-methyl-3-butenoate in a yield of 93%. The NMR spectrum data of the compound thus obtained were identical with those of the compound produced in Example 1.

EXAMPLE 5

A 290 mg quantity of p-methoxybenzyl 2[3-phenylacetamido-4-(2-benzothiazolyldithio)-2-azetidinon-1-yl]3-methyl 3 butenoate and 94 mg of benzenesulfonyl cyanide were dissolved in 3 ml of acetone. To the solution was added 3 mg of sodium benzenesulfinate and the mixture was reacted at room temperature for 2 hours. The acetone was distilled off under reduced pressure and the residue was purified by silica gel column chromatography, giving p-methoxybenzyl 2-(3phenylacetamido 4-benzenesulfonylthio-2- azetidinon-1-yl)-3 methyl 3 butenoate in a yield of 96%. The NMR spectrum data of the compound thus obtained were identical with those of the compound produced in Example 1.

EXAMPLE 6

A 345 mg quantity of p-methoxybenzyl 2-[3-phenylacetamido-4-(2-benzothiazolyldithio)-2-azetidinon-1-yl]-3 methyl 3 butenoate and 112 mg of benzenesulfonyl cyanide were dissolved in 3.5 ml of acetone. To the solution was added 5 mg of benzenesulfinic acid and the mixture was reacted with heating for 8 hours while refluxing the acetone. The acetone was distilled off under reduced pressure and the residue was purified by silica gel column chromatography, giving p-methoxybenzyl 2-(3-phenylacetamido-4-benzene sulfonylthio-2-azetidinon-1-yl)-3-methyl-3-butenoate in a yield of 86%. The NMR spectrum data of the compound thus obtained were identical with those of the compound produced in Example 1.

EXAMPLE 7

A 343 mg quantity of p-methoxybenzyl 2-[3-phenylacetamido-4-(2-benzothiazolyldithio)-2-azetidinon-1 yl]-3 methyl-3-butenoate and 111 mg of benzenesulfonyl cyanide were dissolved in 3.5 ml of ethyl acetate. To the solution was added 5 mg of 2-mercaptobenzothiazole and the mixture was reacted with heating for 8 hours while refluxing the ethyl acetate. The ethyl acetate was distilled off under reduced pressure and the residue was purified by silica gel column chromatography, giving p-methoxybenzyl 2-(3-phenylacet- amido-4-benzenesulfonylthio-2-azetidinon-1-yl)-3-meth- yl-3-butenoate in a yield of 80%. The NMR spectrum data of the compound thus obtained were identical with those of the compound produced in Example 1.

EXAMPLE 8

A 400 mg quantity of p-methoxybenzyl 2-[3-phenylacetamido-4-(2-benzothiazolyldithio)-2-azetidinon-1-yl]-3-methyl-3-butenoate and 130 mg of benzenesulfonyl cyanide were dissolved in 4 ml of tetrahydrofuran. To the solution was added 3 mg of sodium hydroxide and the mixture was reacted at room temperature for 2 hours. The tetrahydrofuran was distilled off under reduced pressure and the residue was dissolved in 10 ml of benzene. The benzene solution was washed with water, dried over Na₂SO₄ and concentrated under reduced pressure. The residue was purified by silica gel column chromatography, giving p-methoxybenzyl 2-(3-phenylacet- amido-4-benzenesulfonylthio-2-azetidinon-1-yl)-3-meth- yl-1-3-butenoate in a yield of 91%. The NMR spectrum data of the compound thus obtained were identical with those of the compound produced in Example 1.

EXAMPLE 9

A 453 mg quantity of p-methoxybenzyl 2-[3-phenylacetamido-4-(2-benzothiazolyldithio)-2-azetidinon-1-yl]-3-methyl-3-butenoate and 147 mg of benzenesulfonyl cyanide were dissolved in 4.5 ml of tetrahydrofuran. To the solution was added 20 µl of a 28% methanol solution of sodium methoxide and the mixture was reacted at room temperature for 50 minutes. The tetrahydrofuran was distilled off under reduced pressure and the residue was dissolved in 10 ml of benzene. The benzene solution was washed with water, dried over Na₂SO₄ and concentrated under reduced pressure. The residue was purified by silica gel column chromatography, giving p-methoxybenzyl 2-(3-phenylacetamido-4-benzenesulfonylthio-2-azetidinon-1-yl)-3-methyl- yl-3-butenoate in a yield of 93%. The NMR spectrum data of the compound thus obtained were identical with those of the compound produced in Example 1.

EXAMPLE 10

A 290 mg quantity of p-methoxybenzyl 2-[3-phenylacetamido-4-(2-benzothiazolyldithio)-2-azetidinon 1-yl]-3-methyl-3-butenoate and 94 mg of benzenesulfonyl cyanide were dissolved in 3 ml of tetrahydrofuran. To the solution was added 3 ml of sodium salt of 2-mercaptobenzothiazole and the mixture was reacted at room temperature for 2 hours. The tetrahydrofuran was distilled off under reduced pressure and the residue was purified by silica gel column chromatography, giving p-methoxybenzyl 2-(3-phenylacetamido-4-benzene- sulfonylthio-2 azetidinon-1-yl)-3-methyl-3-butenoate in a yield of 91%. The NMR spectrum data of the compound thus obtained were identical with those of the compound produced in Example 1.

EXAMPLE 11

A 316 mg quantity of p-methoxybenzyl 2-[3-phenylacetamido-4-(2-benzothiazolyldithio)-2-azetidinon-1-yl]-3-methyl-3-butenoate and 102 mg of benzenesulfonyl cyanide were dissolved in 3 ml of tetrahydrofuran. To the solution was added 5 ml of aniline salt of 2-mercaptobenzothiazole and the mixture was reacted at room temperature for 10 hours. The tetrahydrofuran was distilled off under reduced pressure and the residue was purified by silica gel column chromatography, giving p-methoxybenzyl 2-(3-phenylacetamido-4-benzenesulfonylthio 2-azetidinon-1-yl)-3-methyl-3-butenoate in a yield of 85%. The NMR spectrum data of the compound thus obtained were identical with those of the compound produced in Example 1.

EXAMPLE 12

A 316 mg quantity of p-mechoxybenzyl 2-[3-phenylacetamido-4-(2-benzothiazolyldithio)-2-azetidinon-1-yl]-3-methyl-3-butenoate and 102 mg of benzenesulfonyl cyanide were dissolved in a solvent mixture of 1.5 ml of ethyl acetate and 1.5 ml of methanol. The mixture was reacted with heating for 2 hours while refluxing the solvent. The solvent was distilled off under reduced pressure and the residue was purified by silica gel column chromatography, giving p-methoxybenzyl 2-(3-phenylacetamido-4-benzenesulfonylthio-2-azetidinon 1-yl)-3-methyl-3-butenoate in a yield of 82%. The NMR spectrum data of the compound thus obtained were identical with those of the compound produced in Example 1.

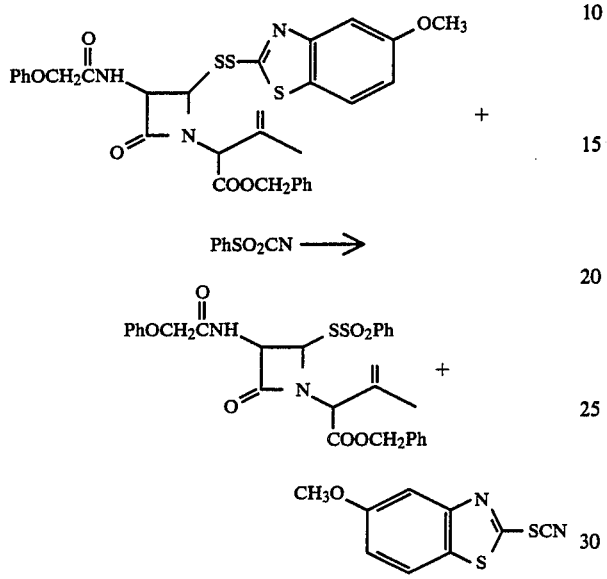

A 250 mg quantity of benzyl 2-[3-phenoxyacetamido-4-(5-methoxybenzothiazol-2-yldithio)-2-azetidinon-1-yl]-3-methyl-3-butenoate and 79 mg of benzenesulfonyl cyanide were dissolved in 2.5 ml of acetone. To the solution was added 3 mg of sodium benzenesulfinate and the mixture was reacted at room temperature for 2 hours. The same subsequent procedure as in Example 5 was followed, producing benzyl 2-(3-phenoxyacetamido-4-benzenesulfonylthio-2-azetidinon-1-yl)-3-methyl-3butenoate in a yield of 93%. The NMR spectrum data of the compound thus obtained were identical with those of the desired compound. Table 2 below shows the NMR spectrum data thereof.

EXAMPLE 14

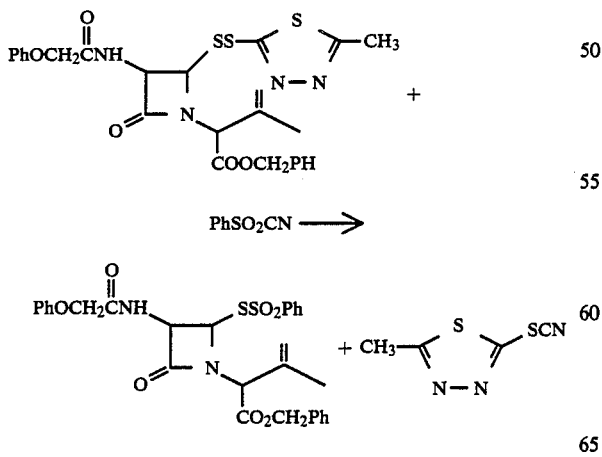

A 255 mg quantity of benzyl 2-[3-phenoxyacetamido-4-(5-methylthiadiazol-2-yldithio)-2-azetidinon-13-methyl-3-butenoate and 90 mg of benzenesulfonyl cyanide were dissolved in 2.5 ml of acetone. To the solution was added 3 mg of sodium benzenesulfinate and the mixture was reacted at room temperature for 2 hours. The same subsequent procedure as in Example 5 was followed, producing benzyl 2-(3-phenoxyacetamido-4-benzenesulfonylthio-2-azetidinon 1-yl -3-methyl-3-butenoate in a yield of 85%. The NMR spectrum data of the compound thus obtained were identical with those of the compound produced in Example 13.

EXAMPLE 15

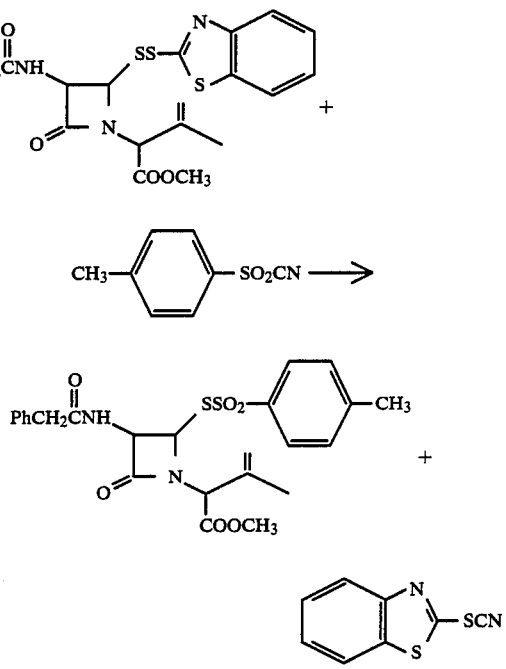

A 480 mg quantity of methyl 2-[3-phenylacetamido-4-(2-benzothiazolyldithio)-2-azetidinon-1-yl]-3-methyl-3-butenoate and 203 mg of p-toluenesulfonyl cyanide were dissolved in 5 ml of acetone. To the solution was added 3 mg of sodium toluenesulfinate and the mixture was reacted at room temperature for 2 hours. The same subsequent procedure as in Example 5 was followed, producing methyl 2-[3-phenylacetamido-4-(p-toluenesulfonylthio)-2-azetidinon-1-yl]-3-methyl-3-butenoate in a yield of 96%. The NMR spectrum data of the compound thus obtained were identical with those of the desired compound. Table 2 below shows the NMR spectrum data of the compound.

EXAMPLE 16

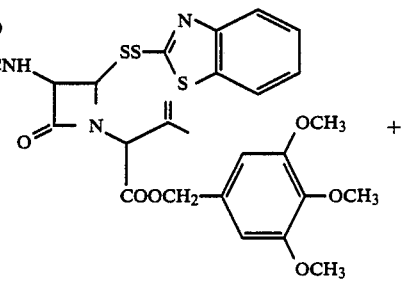

-continued

PhSO₂CN ⟶

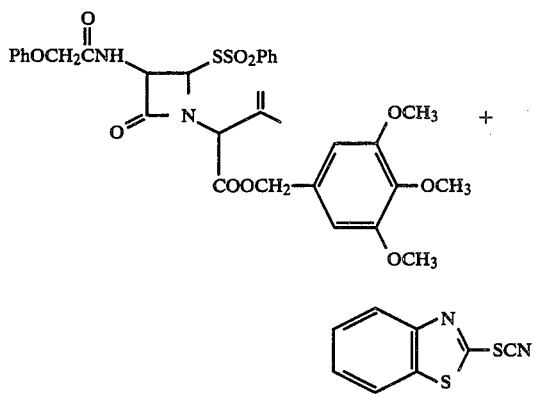

A 210 mg quantity of 3,4,5-trimethoxybenzyl 2-[3-phenoxyacetamido-4-(2-benzothiazolyldithio)-2-azetidinon-1-yl]-3-methyl-3-butenoate and 61 mg of benzenesulfonyl cyanide were dissolved in 2.5 ml of acetone. To the solution was added 3 mg of sodium benzenesulfinate and the mixture was reacted at room temperature for 2 hours. The same subsequent procedure as in Example 5 was followed, producing 3,4,5 trimethoxybenzyl 2-(3-phenoxyacetamido-4-benzenesulfonylthio-2-aze- tidinon-1-yl)-3-methyl-3-butenoate in a yield of 95%. The NMR spectrum data of the compound thus obtained were identical with those of the desired compound. Table 2 shows the NMR spectrum data of the compound.

EXAMPLE 17

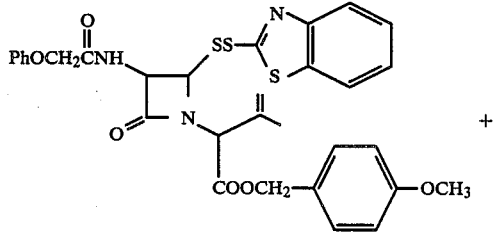

PhSO₂CN ⟶

A 340 mg quantity of p-methoxybenzyl 2-[3-phenoxyacetamido-4-(2-benzothiazolyldithio)-2-azeti- dinon-1-yl]-3-methyl-3-butenoate and 107 mg of benzenesulfonyl cyanide were dissolved in 3.5 ml of acetone. To the solution was added 3 mg of sodium benzenesulfinate and the mixture was reacted at room temperature for 2 hours. The same subsequent procedure as in Example 5 was followed, producing p-methoxybenzyl 2-(3-phenoxyacetamido-4-benzenesulfonylthio-2-azetidinon-1-yl)-3-methyl-3-butenoate in a yield of 90%. The NMR spectrum data of the compound thus obtained which are shown below in Table 2 were identical with those of the desired compound.

EXAMPLE 18

PhSO₂CN ⟶

A 362 mg quantity of benzyl 2-[3-phenoxyacetamido-4-(6-nitrobenzothiazol-2-yldithio)-2-azetidinon-1-yl]-3-methyl-3-butenoate and 112 mg of benzenesulfonyl cyanide were dissolved in 3.5 ml of acetone. To the solution was added 3 mg of sodium benzenesulfinate and the mixture was reacted at room temperature for 2 hours. The same subsequent procedure as in Example 5 was followed, producing benzyl 2-(3-phenoxyacetamido-4-benzenesulfonylthio-2-azetidinon-1-yl)-3-methyl-3-butenoate in a yield of 81%. The NMR spectrum data of the compound thus obtained were identical with those of the compound produced in Example 13.

EXAMPLE 19

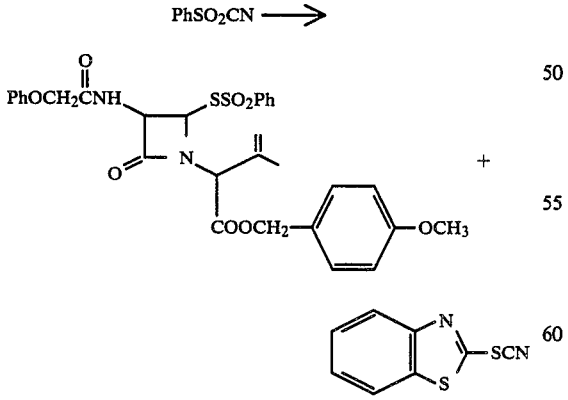

PhSO₂CN ⟶

-continued

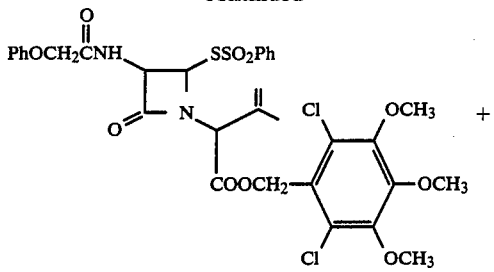

+

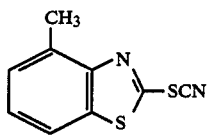

A 268 mg quantity of 3,4,5-trimethoxy-2,6-dichlorobenzyl 2-[3-phenoxyacetamido-4-(4-methylbenzothiazol-2-yldithio)-2-azetidinon-1-yl]-3-methyl-3-butenoate and 69 mg of benzenesulfonyl cyanide were dissolved in 3 ml of acetone. To the solution was added 3 mg of sodium benzenesulfinate and the mixture was reacted at room temperature for 2 hours. The same subsequent procedure as in Example 5 was followed, producing 3,4,5-trimethoxy-2,6 dichlorobenzyl 2-(3-phenoxyacetamido-4-benzenesulfonylthio-2-azetidinon-1-yl)-3-methyl-3-butenoate in a yield of 85%. The NMR spectrum data of the compound thus obtained were identical with those of the desired compound. The NMR spectrum data are shown below in Table 2.

EXAMPLE 20

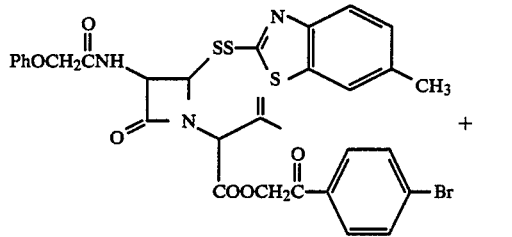

PhSO₂CN ⟶

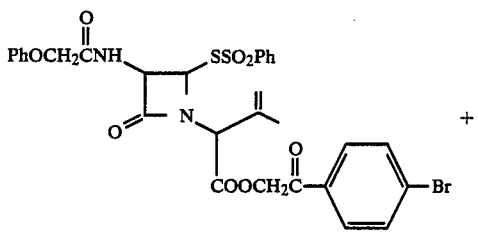

+

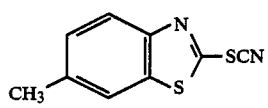

A 412 mg quantity of p bromophenacyl 2-[3-phenoxyacetamido-4-(6-methylbenzothiazol-2-yldithio)-2-azetidinon-1-yl]-3-methyl-3-butenoate and 114 mg of benzenesulfonyl cyanide were dissolved in 4 ml of acetone. To the solution was added 3 mg of sodium benzenesulfinate and the mixture was reacted at room temperature for 2 hours. The same subsequent procedure as in Example 5 was followed, producing p-bromophenacyl 2-(3-phenoxyacetamido-4-benzenesulfonylthio-2-azetidi- non-1-yl)-3-methyl 3-butenoate in a yield of 94%. The NMR spectrum data of the compound thus obtained were identical with those of the desired compound. Table 2 below shows the NMR spectrum data thereof.

EXAMPLE 21

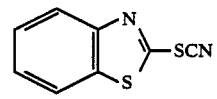

+

PhSO₂CN ⟶

+

A 294 mg quantity of methoxyethoxymethyl 2-[3-phenoxyacetamido-4-(2-benzothiazolyldithio)-2-azetidinon-1-yl]-3-methyl-3-butenoate and 102 mg of benzenesulfonyl cyanide were dissolved in 3 ml of acetone. To the solution was added 3 mg of sodium benzenesulfinate and the mixture was reacted at room temperature for 2 hours. The same subsequent procedure as in Example 5 was followed, producing methoxyethoxymethyl 2-(3-phenoxyacetamido-4-benzenesulfonylthio-2-azetidinon-1-yl)-3-methyl-3-butenoate in a yield of 78%. The NMR spectrum data of the compound thus obtained which are indicated below in Table 2 were identical with those of the desired compound.

EXAMPLE 22

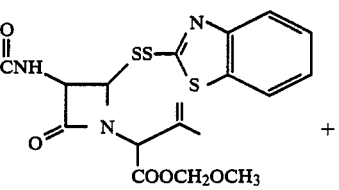

+

PhSO₂CN ⟶

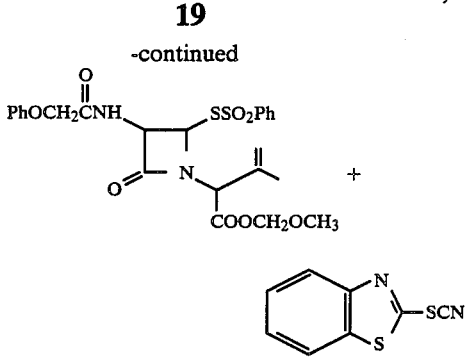

A 305 mg quantity of methoxymethyl 2-[3-phenoxyacetamido-4-(2-benzothiazolyldithio)-2-azetidinon-1-yl]-3-methyl-3-butenoate and 109 mg of benzenesulfonyl cyanide were dissolved in 3 ml of acetone. To the solution was added 3 mg of sodium benzenesulfinate and the mixture was reacted at room temperature for 2 hours. The same subsequent procedure as in Example 5 was followed, producing methoxymethyl 2-(3-phenoxyacet- amido-4-benzenesulfonylthio-2-azetidinon-1-yl)-3-meth- yl-3-butenoate in a yield of 75%. The NMR spectrum data of the compound thus obtained which are shown below in Table 2 were identical with those of the desired compound.

EXAMPLE 23

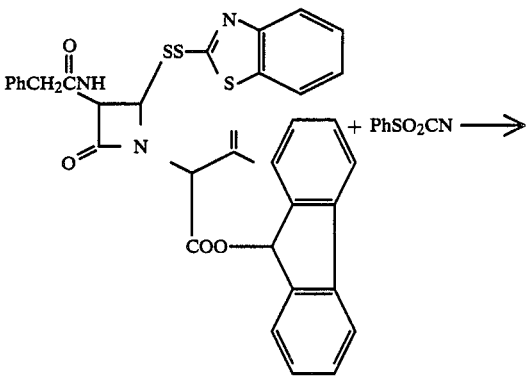

A 372 mg quantity of 9-fluorenyl 2-[3-phenoxyacetamido-4-(2-benzothiazolyldithio)-2-azetidinon-1-yl]-3-methyl-3-butenoate and 110 mg of benzenesulfonyl cyanide were dissolved in 4 ml of acetone. To the solution was added 3 mg of sodium benzenesulfinate and the mixture was reacted at room temperature for 2 hours. The same subsequent procedure as in Example 5 was followed, producing 9-fluorenyl 2-(3-phenoxyacetamido-4-benzenesulfonylthio-2-azetidinon-1-yl)-3-meth- yl-3-butenoate in a yield of 85%. The NMR spectrum data of the compound thus obtained which are shown below in Table 2 were identical with those of the desired compound.

EXAMPLE 24

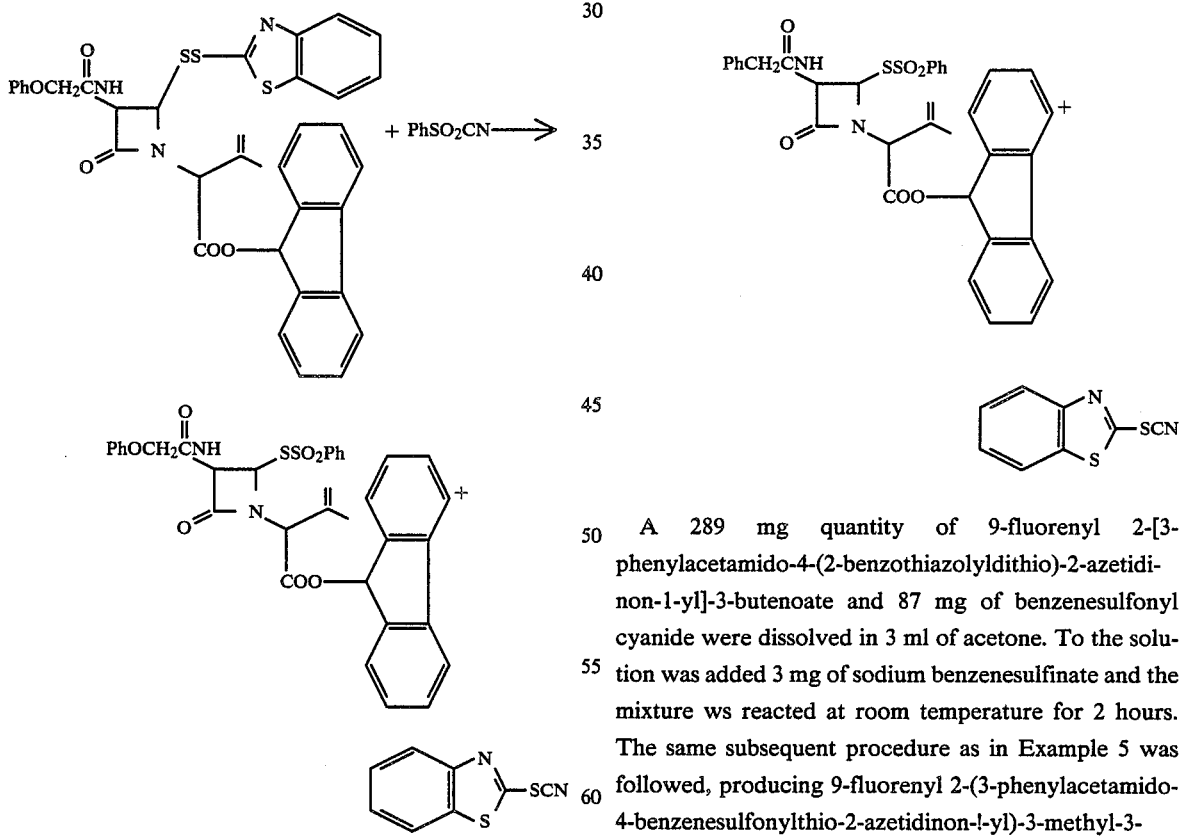

A 289 mg quantity of 9-fluorenyl 2-[3-phenylacetamido-4-(2-benzothiazolyldithio)-2-azetidinon-1-yl]-3-butenoate and 87 mg of benzenesulfonyl cyanide were dissolved in 3 ml of acetone. To the solution was added 3 mg of sodium benzenesulfinate and the mixture ws reacted at room temperature for 2 hours. The same subsequent procedure as in Example 5 was followed, producing 9-fluorenyl 2-(3-phenylacetamido-4-benzenesulfonylthio-2-azetidinon-!-yl)-3-methyl-3-butenoate ina yield of 90%. The NMR spectrum data of the compound thus obtained which are shown below in Table 2 were identical with those of the desired compound.

EXAMPLE 25

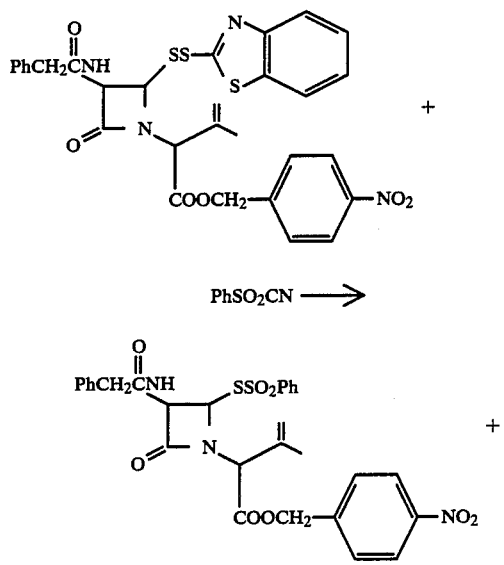

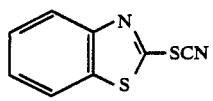

A 310 mg quantity of o-nitrobenzyl 2-[3-phenylacetamido-4-(2-benzothiazolyldithio)-2-azetidinon-1cyanide were dissolved in 3 ml of acetone. To the solution was added 3 mg of sodium benzenesulfinate and the mixture was reacted at room temperature for 2 hours. The same subsequent procedure as in Example 5 was followed, producing o-nitrobenzyl 2-(3-phenylacetamido-4-benzenesulfonylthio-2-azetidinon-1-yl)-3-methyl-3-butenoate in a yield of 93%. The NMR spectrum data of the compound thus obtained which are shown below in Table 2 were identical with those of the desired compound.

EXAMPLE 27

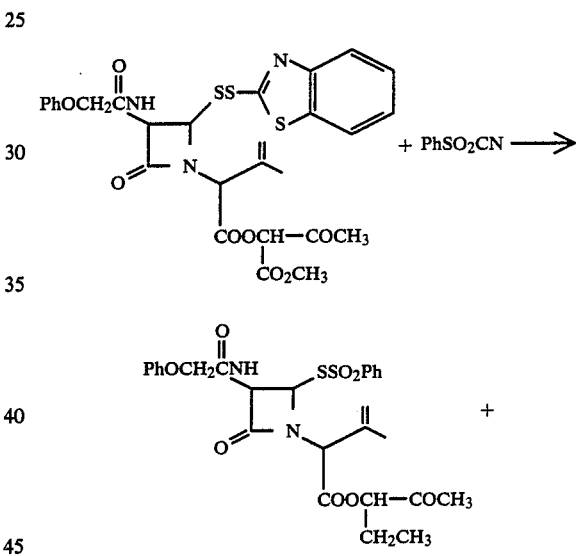

A 250 mg quantity of p-nitrobenzyl 2-[3-phenylacetamido-4-(2-benzothiazolyldithio)-2-azetidinon-1-yl]-3-methyl-3-butenoate and 79 mg of benzenesulfonyl cyanide were dissolved in 2.5 ml of acetone. To the solution was added 3 mg of sodium benzenesulfinate and the mixture wasa reacted at room temperature for 2 hours. The same subsequent procedure as in Example 5 was followed, producing p-nitrobenzyl 2-(3-phenylactamido-4-benzenesulfonylthio-2-azetidinon-1-yl)-3-methyl-3-butenoate in a yield of 94%. The NMR spectrum data of the compound thus obtained which are shown below in Table 2 were identical with those of the desired compound.

EXAMPLE 26

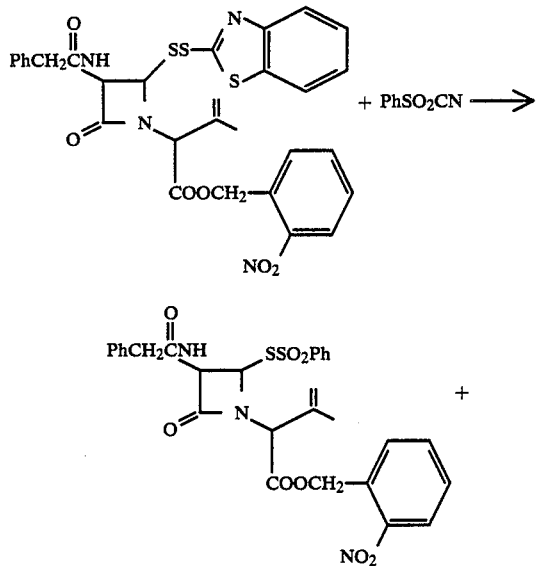

A 352 mg quantity of 1-methoxycarbonyl-2-oxopropyl 2-[3-phenoxyacetamido-4-(2-benzothiazolyldithio)-2-azetidinon-1-yl]-3-methyl-3-butenoate and 112 mg of benzenesulfonyl cyanide were dissolved in 3.5 ml of acetone. To the solution was added 3 mg of sodium benzenesulfinate an the mixture was reacted at room temperature for 2 hours. The same subsequent procedure as in Example 5 was followed, producing l-methoxycarbonyl-2-oxopropyl 2-(3-phenoxyacetamido-4-benzenesulfonylthio-2-azetidinon-1-yl-3-methyl-3-butenoate in a yield of 90%. The NMR spectrum data of the compound thus obtained which are shown below in Table 2 were identical with those of the desired compound.

EXAMPLE 28

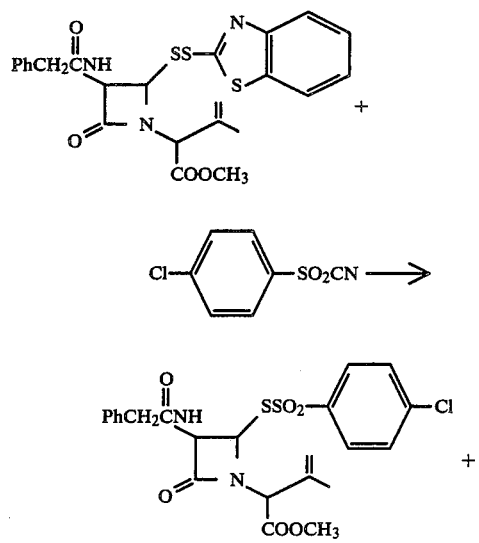

A 180 mg quantity of methyl 2-[3-phenylacetamido-4-(2-benzothiazolyldithio)-2-azetidinon-1-yl]-3-methyl-3-butenoate and 85 mg of p-chlorobenzenesulfonyl cyanide were dissolved in 2 ml of acetone. To the solution was added 3 mg of sodium p-chlorobenzenesulfinate and the mixture was reacted at room temperature for 2 hours. The same subsequent procedure as in Example 5 was followed, producing methyl 2-[3-phenylactamido-4-(p-chlorobenzenesulfonylthio)-2-azetidinon-1-yl]-3-methyl-3-butenoate in a yield of 86% The NMR spectrum data of the compound thus obtained which are shown below in Table 2 were identical with those of the desired compound.

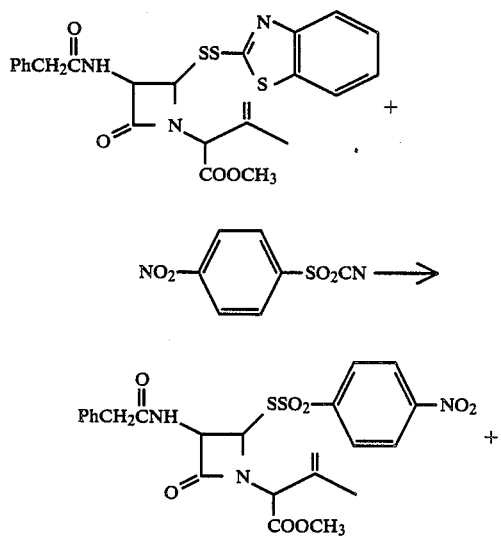

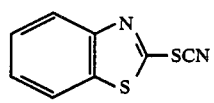

A 203 mg quantity of methyl 2-[3-phenylacetamido-4-(2-benzothiazolyldithio)-2-azetidinone-1-yl]-3-methyl-3-butenoate and 101 mg of p-nitrobenzenesulfonyl cyanide were dissolved in 2 ml of acetone. To the solution was added 3 mg of sodium p-nitrobenzenesulfinate and the mixture was reacted at room temperature for 2 hours. The same subsequent procedure as in Example 5 was followed, producing methyl 2-[3-phenylacetamido-4-(p-nitrobenzenesulfonylthio)-2-azetidinone-1-yl]-3-methyl-3-butenoate in a yield of 73%. The NMR spectrum data of the compound thus obtained which are shown below in Table 2 were identical with those of the desired compound.

EXAMPLE 30

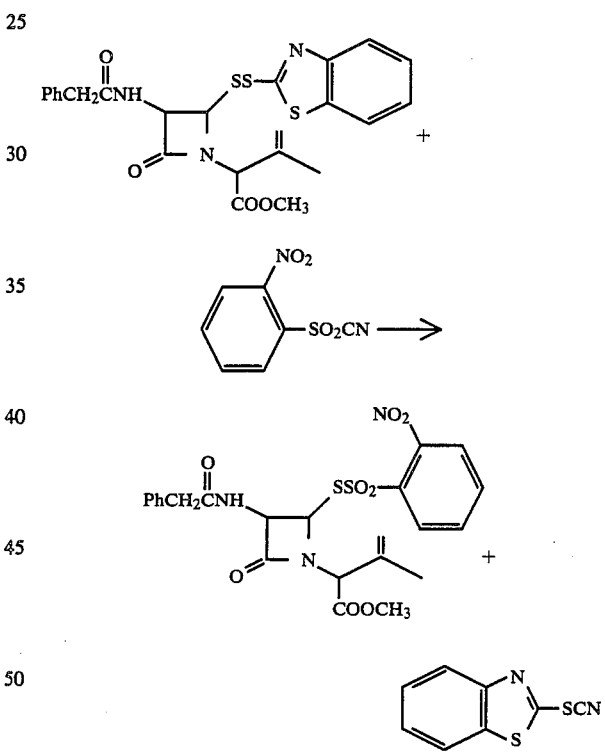

A 231 mg quantity of methyl 2-[3-phenylacetamido-4-(2-benzothiazolyldithio)-2-azetidinon-1-yl]-3-methyl-3-butenoate and 115 mg of o-nitrobenzenesulfonyl cyanide were dissolved in 2.5 ml of acetone. To the solution was added 3 mg of sodium benzenesulfinate and the mixture was reacted at room temperature for 2 hours. The same subsequent general procedure as in Example 5 was followed, producing methyl 2-[3-phenylactanido-4-(o-nitrobenzenesulfonylthio)-2-azetidinon-1-yl]-3-methyl-3-butenoate in a yield of 70%. The NMR spectrum data of the compound thus obtained were identical with those of the desired compound. Table 2 below shows the data thereof.

EXAMPLE 31

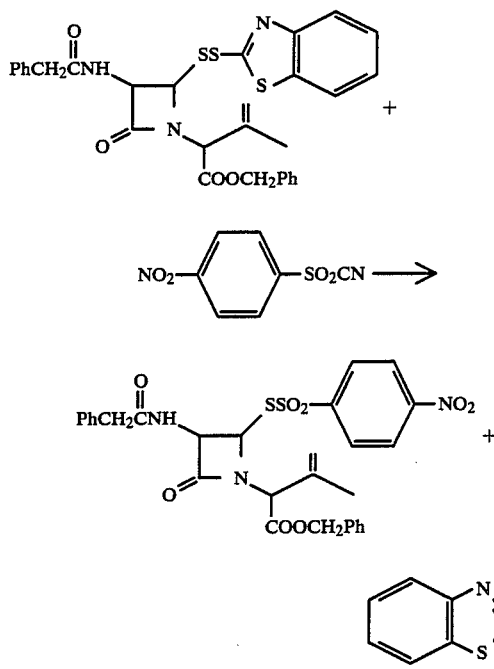

A 308 mg quantity of benzyl 2-[3-phenylacetamido-4-(2-benzothiazolyldithio)-2-azetidinon-1-yl-3-methyl-3-butenoate and 133 mg of p-nitrobenzenesulfonyl cyanide were dissolved in 3 ml of acetone. To the solution was added 0.3 ml of water and the mixture was reacted with heating for 2 hours while refluxing the acetone. The same subsequent general procedure as in Example 1 was followed, producing benzyl 2-[3-phenylacetamido-4-(p-nitrobenzenesulfonylthio-2-azetidinon-1-yl]-3-methyl-3-butenoate in a yield of 77%. The NMR spectrum data of the compound thus obtained which are shown below in Table 2 were identical with those of the desired compound.

EXAMPLE 32

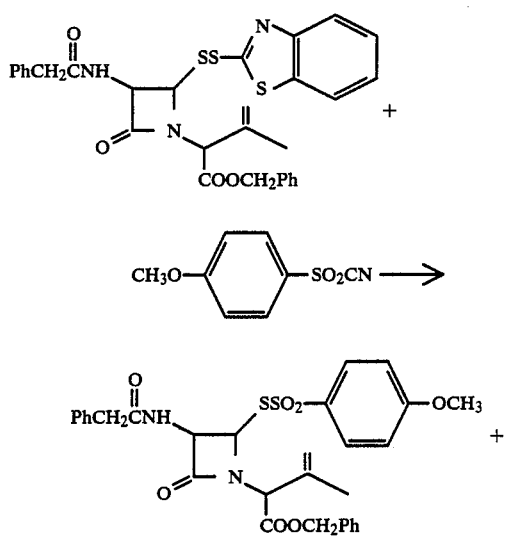

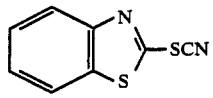

A 189 mg quantity of benzyl 2-[3-phenylacetamido-4-(2-benzothiazolyldithio)-2-azetidinon-1-yl]-3-methyl-3-butenoate and 76 mg of p-methoxybenzenesulfonyl cyanide were dissolved in 2 ml of acetone. To the solution was added 0.2 ml of water and the mixture was reacted with heating for 2 hours while refluxing the acetone. The same subsequent general procedure as in Example 1 was followed, producing benzyl 2-[3-phenylacetamido-4-(p-methoxybenzenesulfonylthio)-2-azetidinon-1-yl]-3-methyl-3-butenoate in a yield of 93%. The NMR spectrum data of the compound thus obtained which are shown below in Table 2 were identical with those of the desired compound.

EXAMPLE 33

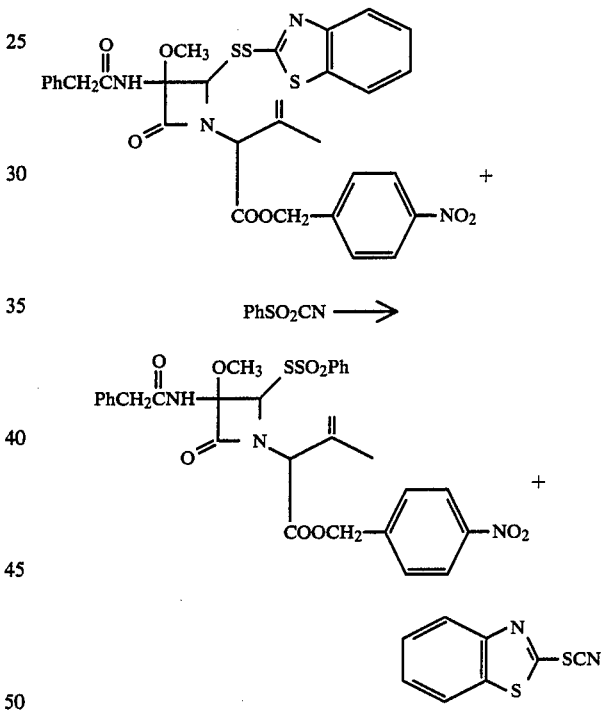

A 315 mg quantity of p-nitrobenzyl 2-[3-methoxy-3-phenylacetamido-4-(2-benzothiazolyldithio)-2-azetidinon-1-yl]-3-methyl-3-butenoate and 95 mg of benzenesulfonyl cyanide were dissolved in 3 ml of acetone. To the solution was added 3 mg of sodium benzenesulfinate and the mixture was reacted at room temperature for 2 hours. The same subsequent general procedure as in Example 5 was followed, producing p-nitrobenzyl 2-(3-methoxy-3-phenylacetamido-4-benzenesulfonylthio-2-azetidinon-1-yl)-3-methyl-3-butenoate in a yield of 88%. The NMR spectrum data of the compound thus obtained which are shown below in Table 2 were identical with those of the desired compound.

EXAMPLES 34 to 36

The general procedure of Example 1 was repeated, producing the compounds as shown below in Table 1.

The NMR spectrum data of these compounds are listed below in Table 2.

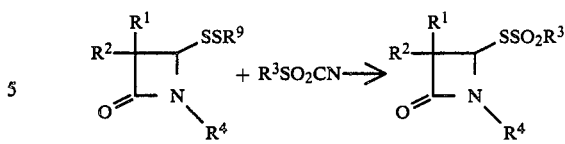

TABLE 1

| Ex. No. | R¹ | R² | R⁹ | R⁴ | R³ | Yield (%) |
|---|---|---|---|---|---|---|
| 34 | H | PhCH₂C(O)NH— | benzothiazol-2-yl | CH₃-CH(CH₃)-C(=)—COOCH₂CCl₃ | 4-CH₃-C₆H₄— | 94 |
| 35 | " | " | " | " | 4-CH₃O-C₆H₄— | 95 |
| 36 | " | " | " | H | 4-CH₃-C₆H₄— | 78 |

TABLE 2

| R¹ | R² | R⁴ | R³ | NMR(CDCl₃, δ, J=Hz) |
|---|---|---|---|---|
| H | PhCH₂C(O)NH— | CH₂=C(CH₃)-CH-COOCH₂-C₆H₄-OCH₃ | Ph | 1.71(s,3H),3.54(s,2H),3.78(s,3H),4.45(s,1H), 4.69(s,1H),4.72(bs,1H),5.02(s,1H),5.06(dd,1H, J=4.0 and 6.5),5.70(d,1H,J=4.0),5.90(d,1H, J=6.5),6.82(d,2H,J=7.0),7.00–7.85(m,12H) |
| H | PhOCH₂C(O)NH— | CH₂=C(CH₃)-CH-COOCH₂Ph | Ph | 1.78(s,3H),4.37 and 4.42(ABq,2H,J=12.0), 4.55(s,1H),4.79(s,1H),4.82(bs,1H),5.14(s,2H), 5.27(dd,1H,J=4.0 and 7.0),5.87(d,1H,J=4.0), 6.75–7.90(m,16H) |
| H | PhCH₂C(O)NH— | CH₂=C(CH₃)-CH-COOCH₃ | 4-CH₃-C₆H₄— | 1.74(s,3H),2.40(s,3H),3.50(s,2H),3.71(s,3H), 4.64(s,1H),4.70(s,1H),4.89(s,1H),5.05(dd,1H, J=5 and 8),5.78(d,1H,J=5),6.52(d,H,J=8), 7.22(s,5H),7.30(d,2H,J=9),7.68(d,2H,J=9) |
| H | PhOCH₂C(O)NH— | CH₂=C(CH₃)-CH-COOCH₂-(3,4,5-triOCH₃-C₆H₂) | Ph | 1.79(s,3H),3.85(s,9H),4.35 and 4.41(ABq,2H, J=12.5),4.62(s,1H),4.80(s,1H),4.84(bs,1H), 5.08(s,2H),5.26(dd,1H,J=4 and 7),5.84(d,1H, J=4),6.54(s,2H),6.75–7.90(m,11H) |

TABLE 2-continued

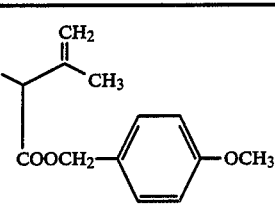

| R¹ | R² | R⁴ | R³ | NMR(CDCl₃, δ, J=Hz) |
|---|---|---|---|---|
| H | PhOCH₂CONH— | 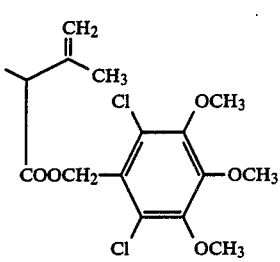 | Ph | 1.76(s,3H),3.77(s,3H),4.34 and 4.40(ABq,2H, J=12),4.53(s,1H),4.76(s,1H),4.79(bs,1H), 5.07(s,2H),5.27(dd,1H,J=4 and 6.5),5.86(d,1H, J=4),6.65–7.90(m,15H) |
| H | PhOCH₂CONH— | 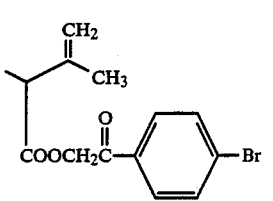 | Ph | 1.76(s,3H),3.89(s,6H),3.94(s,3H),4.36 and 4.41(ABq,2H,J=12),4.60(s,1H),4.78(bs,1H), 4.80(s,1H),5.24(dd,1H,J=4 and 6.5),5.38(s,2H), 5.88(s,2H),6.75–7.90(m,11H) |
| H | PhOCH₂CONH— | 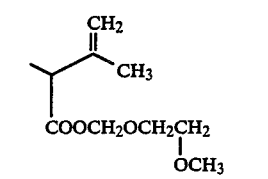 | Ph | 1.85(s,3H),4.38 and 4.44(ABq,2H,J=12),4.90(s, 1H),4.96(s,2H),5.28 and 5.34(ABq,2H,J=12), 5.35(dd,1H,J=4 and 6.5),5.85(d,1H,J=4), 6.75–7.95(m,15H) |
| H | PhOCH₂CONH— | 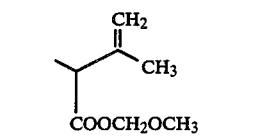 | Ph | 1.82(s,3H),3.36(s,3H),3.40–3.65(m,2H),3.65– 3.90(m,2H),4.36 and 4.41(ABq,2H,J=12), 4.69(s,1H),4.79(s,1H),4.94(bs,1H),5.15–5.60(m, 3H),5.90(d,1H,J=4),6.75–8.00(m,11H) |
| H | PhOCH₂CONH— | 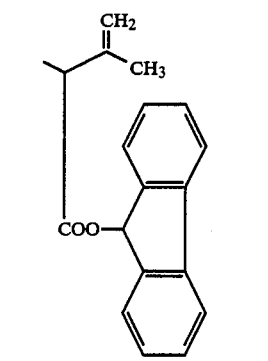 | Ph | 1.85(s,3H),3.46(s,3H),4.41 and 4.46(ABq,2H, J=12),4.71(s,1H),4.82(s,1H),4.95(bs,1H),5.10– 5.40(m,3H),5.91(d,1H,J=4.7),6.80–8.00(m,1H) |
| H | PhOCH₂CONH— |  | Ph | 1.78(s,3H),4.39 and 4.44(ABq,2H,J=12),4.76(s, 1H),4.85(s,1H),4.88(bs,1H),5.34(dd,1H, J=4.7 and 8.2),5.87(d,1H,J=4.7),6.76(s,1H), 6.80–7.90(m,19H) |

TABLE 2-continued

| R¹ | R² | R⁴ | R³ | NMR(CDCl₃, δ, J=Hz) |
|---|---|---|---|---|
| H | PhCH₂C(O)NH— | CH₂=C(CH₃)CH(—)CH₂COO-CH(fluorenyl) | Ph | 1.76(s,3H),3.57(s,2H),4.71(s,1H),4.82(s,1H), 4.84(s,1H),5.16(dd,1H,J=4.7 and 8.1),5.76(d, 1H,J=4.7),6.50(d,1H,J=8.1),6.74(s,1H),7.05–7.90(m,18H) |
| H | PhCH₂C(O)NH— | CH₂=C(CH₃)CH(—)COOCH₂-(4-NO₂-C₆H₄) | Ph | 1.78(s,3H),3.56(s,2H),4.57(s,1H),4.76(s,1H), 4.88(bs,1H),5.11(dd,1H,J=4 and 7),5.23(s,2H), 5.72(d,1H,J=4),6.06(d,1H,J=7),7.00–8.00(m, 12H),8.19(d,2H,J=7) |
| H | PhCH₂C(O)NH— | CH₂=C(CH₃)CH(—)COOCH₂-(2-NO₂-C₆H₄) | Ph | 1.78(s,3H),3.56(s,2H),4.60(s,1H),4.76(s,1H), 4.87(bs,1H),5.12(dd,1H,J=4 and 6.5),5.53(s,2H),5.64(d,1H,J=4), 6.20(d,1H,J=6.5),7.10–8.20(m,14H) |
| H | PhOCH₂C(O)NH— | CH₂=C(CH₃)CH(—)COOCH(COCH₃)(CO₂CH₃) | Ph | 1.84(s,3H),2.35(s,3H),3.83(s,3H),4.38 and 4.45(ABq,2H,J=11),4.80–5.05(m,3H),5.38(dd, 1H,J=4 and 7),5.55(s,1H),5.85(d,1H,J=4.0), 6.75–8.00(m,11H) |
| H | PhCH₂C(O)NH— | CH₂=C(CH₃)CH(—)COOCH₃ | 4-Cl-C₆H₄ | 1.78(s,3H),3.51(bs,2H),3.70(s,3H),4.61(bs,1H), 4.76(s,1H),4.86(bs,1H),5.06(dd,1H,J=5 and 8), 5.83(d,1H,J=5),7.14(d,1H,J=8),7.23(s,5H), 7.43(d,2H,J=8),7.81(d,2H,J=8) |
| H | PhCH₂C(O)NH— | CH₂=C(CH₃)CH(—)COOCH₃ | 4-NO₂-C₆H₄ | 1.80(s,3H),3.52(bs,2H),3.70(s,3H),4.55(bs,1H), 4.79(s,1H),4.87(bs,1H),5.03(dd,1H,J=5 and 8), 5.87(d,1H,J=5),6.73(d,1H,J=8),7.22(s,5H), 7.94(d,2H,J=9),8.24(d,2H,J=9) |
| H | PhCH₂C(O)NH— | CH₂=C(CH₃)CH(—)COOCH₃ | 2-NO₂-C₆H₄ | 1.80(s,3H),3.48(bs,2H),3.70(s,3H),4.64(bs,1H), 4.80(s,1H),4.88(bs,1H),5.13(dd,1H,J=5 and 8), 6.06(d,1H,J=5),6.88(d,1H,J=8),7.17(s,5H), 7.60–8.20(m,4H) |

TABLE 2-continued

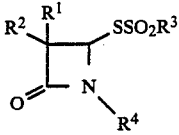

| R¹ | R² | R⁴ | R³ | NMR(CDCl₃, δ, J=Hz) |
|---|---|---|---|---|
| H | PhCH₂C(O)NH— | CH₂=C(CH₃)—, COOCH₂Ph | p-NO₂-C₆H₄ | 1.75(s,3H),3.50(s,2H),4.76(bs,1H),4.84(s,1H), 4.92(bs,1H),5.10(dd,1H,J=5 and 8),5.12(s,2H), 5.92(d,1H,J=5),6.91(d,1H,J=8),7.20(s,5H), 7.30(s,5H),7.87(d,2H,J=9),8.18(d,2H,J=9) |
| H | PhCH₂C(O)NH— | CH₂=C(CH₃)—, COOCH₂Ph | p-OCH₃-C₆H₄ | 1.75(s,3H),3.50(s,2H),3.79(s,3H),4.65(bs,1H), 4.77(s,1H),4.85(bs,1H),5.12(dd,1H,J=5 and 8), 5.13(s,2H),5.73(d,1H,J=5),6.63(d,1H,J=8), 6.87(d,2H,J=9),7.20(s,5H),7.29(s,5H), 7.67(d,2H,J=9) |
| CH₃O— | PhCH₂C(O)NH— | CH₂=C(CH₃)—, COOCH₂-C₆H₄-NO₂ | Ph | 1.79(s,3H),3.46(s,3H),3.61(s,2H),4.57(s,1H), 4.81(s,1H),4.88(bs,1H),5.23(s,2H),5.29(s,1H), 6.00(bs,1H),7.10-7.90(m,12H),8.17(d,2H,J=9) |
| H | PhCH₂C(O)NH— | (CH₃)₂C=C(CH₃)—, COOCH₂CCl₃ | p-CH₃-C₆H₄ | 1.91(s,3H),2.15(s,3H),3.60(s,2H),4.60-4.80(m, 3H),5.83(d,1H,J=5Hz),7.20(m,8H),7.66(d,2H, J=9Hz) |
| H | PhCH₂C(O)NH— | (CH₃)₂C=C(CH₃)—, COOCH₂CCl₃ | p-OCH₃-C₆H₄ | 1.90(s,3H),2.13(s,3H),3.50(s,2H),3.75(s,3H), 4.60-4.80(m,3H),5.85(d,1H,J=4.5Hz),6.84(d, 2H,J=7Hz),7.20(m,6H),7.77(d,2H,J=7Hz) |
| H | PhCH₂C(O)NH— | H | p-CH₃-C₆H₄ | 2.50(s,3H),3.63(s,2H),5.20-5.50(m,2H),7.20-7.80(m,11H) |

We claim:

1. A process for preparing an azetidinone derivative represented by the formula

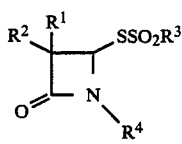

(I)

wherein R¹ is hydrogen, halogen or lower alkoxy, R² is hydrogen, a halgen, lower alkoxy, amino or a group

NHCR⁵
‖
O (in which R⁵ is substituted or unsubstituted phenyl, substituted or unsubstituted phenylmethyl, substituted or unsubstited phenoxymethyl, or substituted or unsubstituted benzoyl), or R¹ and R², when taken together with the carbon atom in the azetidinone ring, are carbonyl, R³ is substituted or unsubstituted phenyl, and R⁴ is hydrogen or one of the following groups

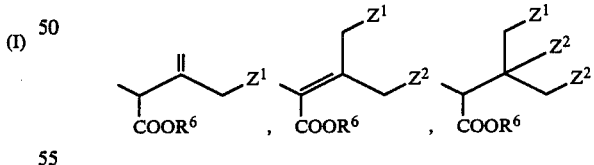

(in which R⁶ is hydrogen or a carboxy protecting group, and Z¹ and Z² are the same or different and reprsent hydrogen, a halogen, C₁-C₄ alkylthio, phenylthio optionally substituted with 1 to 5 nitro groups or halogen atoms on the phenyl ring, 2-pyridylthio, 2-benzothiadiazolylthio, 1,3,4-thiadiazol-5-ylthio, 1,2,3,4-tetrazol-5-ylthio, O-ethyldithiocarbonate, N,N-diethyldithiocarbamate, phenyl-sulfonyl, p-methylphenylsulfonyl, hydroxy, C₁-C₄ alkoxy, C₁-C₄ acyloxy, benzoyloxy, nitrosoxy, diphenylphosphonyloxy, methanesulfonate, diphenylmethyloxy, di(C₁-C₄ alkyl)amino or piperidin-1-yl), the process comprising reacting a dithioazetidinone derivative represented by the formula

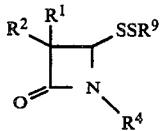

(VI)

wherein $R^1$, $R^2$ and $R^4$ are as defined above and $R^9$ is a substituted or unsubstituted, nitrogen-containing aromatic heterocyclic residue with a compound represented by the formula $$R^3SO_2CN \quad (VII)$$

wherein $R^3$ is as defined above.

2. A process as defined in claim 1 in which $R^1$ in the dithioazetidinone derivative of the formula (VI) is hydrogen, F, Cl, Br, I or $C_1$-$C_4$ alkoxy, $R^2$ is hydrogen, F, Cl, Br, I, $C_1$-$C_4$ alkoxy, amino or a group

in which $R^5$ is phenyl, phenyl having 1 to 3 substituents selected from the group consisting of $C_1$-$C_4$ alkyl, F, Cl, Br, I, $C_1$-$C_4$ alkoxy and nitro on the phenyl ring, phenylmethyl, phenylmethyl having 1 to 3 substituents selected from the group consisting of $C_1$-$C_4$ alkyl, F, Cl, Br, I, $C_1$-$C_4$ alkoxy and nitro on the phenyl ring, phenylmethyl having methylene substituted with halognen, hydroxy, hydroxyimino, $C_1$-$C_4$ alkoxyimino or amino, phenoxymethyl, phenoxymethyl having 1 to 3 substituents selected from the group consisting of $C_1$-$C_4$ alkyl, F, Cl, Br, I, $C_1$-$C_4$ alkoxy and nitro on the phenyl ring, benzoyl, or benzoyl having 1 to 3 substituents selected from the group consisting of $C_1$-$C_4$ alkyl, F, Cl, Br, I, $C_1$-$C_4$ alkoxy and nitro on the phenyl ring, or $R^1$ or $R^2$ are carbonyl when taken together with the carbon atom in the azetidinone ring, $R^4$ is as defined in claim 1 and $R^9$ is said heterocyclic residue selected from the group consisting of thiazol-2-yl, thiadiazol-2-yl, benzothiazol-2-yl, benzoxazol-2-yl, benzimidazol-2-yl, pyrimidin-2-yl and 2-pyridyl, or said heterocyclic residue having 1 to 3 substituents selected from the group consisting of $C_1$-$C_4$ alkyl, phenyl, $C_1$-$C_4$ alkoxy, nitro and halogen.

3. A process as defined in claim 1 in which $R^3$ in the compound of the formula (VII) is phenyl or phenyl having 1 to 3 substituents selected from the group consisting of $C_1$-$C_4$ alkyl, F, Cl, Br, I, $C_1$-$C_4$ alkoxy and nitro on the phenyl ring.

4. A process as defined in any one of claims 1 to 3 in which about 1 to about 5 moles of the compound of the formula (VII) is used per mole of the compound of the formula (VI).

5. A process as defined in any one of claims 1 to 3 in which the reaction system contains as a catalyst at least one compound selected from: p1 (a) a sulfinic acid represented by the formula $$R^3SO_2H \quad (VIII)$$

(wherein $R^3$ is as defined above) or a salt thereof.
(b) a thiol represented by the formula $$R^9SH \quad (IX)$$

(wherein $R^9$ is as defined above) or a salt thereof and (c) a nucleophilic compound selected from the group consisting of water, alkali metal hydroxide, alcohol having 1 to 4 carbon atoms or a salt thereof, phenol optionally substituted with methyl, methoxy or nitro or a salt thereof, lower alkyl thiol or a salt thereof, thiophenol optionally substituted with methyl or nitro or a salt thereof, lower alkyl sulfinic acid or a salt thereof, and lower alkyl carboxylic acid or a salt thereof.

6. A process as defined in claim 5 in which the catalyst is used in an amount of about 0.0001 to about 0.1 mole per mole of the compound of the formula (VI).

7. A process as defined in claim 6 in which the reaction is conducted at a temperature ranging from $-20°$ C. to the temperature at which the solvent used is refluxed.

* * * * *